United States Patent [19]

Campbell et al.

[11] Patent Number: 5,733,732
[45] Date of Patent: Mar. 31, 1998

[54] METHODS FOR DETECTING PRIMARY ADHALINOPATHY

[75] Inventors: Kevin P. Campbell, Iowa City, Iowa; Steven L. Roberds, Mattawan, Mich.; Yoshihide Sunada, Iowa City, Iowa; Federica Piccolo, Paris, France; Marc Jeanpierre, Bourg la Reine, France; Jean-Claude Kaplan, Paris, France

[73] Assignee: University of Iowa Research Foundation, Iowa City, Iowa

[21] Appl. No.: 582,539

[22] Filed: Jan. 3, 1996

[51] Int. Cl.[6] .......... C12Q 1/68; C07H 19/00; C07H 21/02; C07H 21/04
[52] U.S. Cl. .......... 435/6; 536/22.1; 536/23.1; 536/23.5; 536/24.3
[58] Field of Search .......... 435/6; 536/22.1, 536/23.1, 23.5, 24.3

[56] References Cited

U.S. PATENT DOCUMENTS

| | | | |
|---|---|---|---|
| 5,270,163 | 12/1993 | Gold et al. | 435/6 |
| 5,362,631 | 11/1994 | Calabretta | 435/69.5 |
| 5,420,029 | 5/1995 | Gelfand et al. | 435/194 |

FOREIGN PATENT DOCUMENTS

| | | | |
|---|---|---|---|
| 349435 | 1/1990 | European Pat. Off. | C12P 21/02 |
| 403384 | 12/1990 | European Pat. Off. | C12Q 1/70 |
| 4140381 | 6/1993 | European Pat. Off. | C07K 7/10 |
| 591914 | 4/1994 | European Pat. Off. | C12N 7/00 |
| 594959 | 4/1994 | European Pat. Off. | C12Q 1/68 |
| WO 86 04094 | 7/1986 | WIPO | C12P 21/00 |
| WO 8907146 | 8/1989 | WIPO | C12N 15/00 |
| WO 920264 | 2/1992 | WIPO | C12Q 1/68 |
| WO 9213103 | 8/1992 | WIPO | C12Q 1/68 |
| WO 9219771 | 11/1992 | WIPO | C12Q 1/68 |
| WO 9313114 | 7/1993 | WIPO | C07H 15/12 |
| WO 9314188 | 7/1993 | WIPO | C12N 5/00 |
| WO 9419473 | 9/1994 | WIPO | C12N 15/67 |

OTHER PUBLICATIONS

Roberds et al. "Missense Mutations in the Adhalin Gene linked to Autosomal Recessive Muscular Dystrophy", Cell, vol. 78, pp. 625–633, Aug. 1994.
McNally et al., Proc. Natl. Acad. Sci. USA 91: 9690 (1994).
Romero et al., C.R. Acad. Sci. Paris 317: 70 (1994).
Matsumara et al., Nature 359: 320 (1992).
Piccolo, F., et al., Nature Genetics, 10: 243 (1995).

Primary Examiner—Ardin H. Marschel
Assistant Examiner—Jezia Riley
Attorney, Agent, or Firm—Kevin M. Farrell

[57] ABSTRACT

Disclosed herein are compositions and methods for the detection of primary adhalinopathy. More specifically, disclosed herein are nucleic acid probes which hybridize specifically, under stringent hybridization conditions, to a mutant adhalin gene or the complement thereof, but not to the corresponding region of a wild-type adhalin gene. Also disclosed are methods for the detection of a mutation in the human adhalin gene which is responsible for primary adhalinopathy. Such methods include the use of the nucleic acid probes of the invention for detection of the myopathy by hybridization, as well as detection by direct DNA sequencing techniques.

1 Claim, 1 Drawing Sheet

METHODS FOR DETECTING PRIMARY ADHALINOPATHY

BACKGROUND OF THE INVENTION

Autosomal recessive muscular dystrophies are clinically heterogeneous. The most severe forms were first described in Tunisian families and called SCARMD for severe childhood autosomal recessive muscular dystrophy. Because the disease resembles Duchenne muscular dystrophy but affects both males and females it has also been coined Duchenne-like autosomal recessive muscular dystrophy (MIM#253700). Other cases were also reported in Sudan and in the Arabic peninsula. In SCARMD patients, adhalin, the 50 kDa glycoprotein belonging to the sarcolemmal complex of dystrophin-associated proteins, is missing whereas dystrophin is present. Adhalin deficiency has been found in SCARMD patients from North Africa, Europe, Brazil, Japan and North America. In families from Tunisia, Algeria and Morocco linkage analysis assigned a SCARMD locus to the proximal part of chromosome 13q. However the chromosome 13 locus was excluded in some families from Brazil, and in one family from France, indicating genetic heterogeneity of this condition. Thus, there are two kinds of myopathies with adhalin deficiency: one with a primary defect of adhalin (primary adhalinopathies), and one in which absence of adhalin is secondary to a separate gene defect on chromosome 13.

The human adhalin gene was recently cloned and assigned to chromosome 17q21 (Roberds et al., Cell 78:625 (1994); McNally et al., Proc. Natl. Acad. Sci. USA 91:9690 (1994)). It became thus possible to investigate its possible implication in SCARMD cases not linked to chromosome 13. Indeed in one such family a tight linkage of the disease to the adhalin locus was demonstrated, and ultimately the patients were found to be compound heterozygotes for missense mutations in the adhalin gene (Roberds et al., Cell 78:625 (1994)). This gene was therefore validated as the site of the primary defect in at least one family. This opened the question of the relative frequency of primary adhalinopathies, with defects in the adhalin gene itself, versus secondary adhalinopathies, in which the adhalin deficiency is secondary to another, still unknown, gene defect, such as the one carried by chromosome 13. The identification of specific mutations resulting in primary adhalinopathy would facilitate the diagnosis of the myopathy.

SUMMARY OF THE INVENTION

The subject invention relates to compositions and methods for the detection of primary adhalinopathy. In one aspect, the invention relates to nucleic acid probes which hybridize specifically, under stringent hybridization conditions, to a mutant adhalin gene or the complement thereof, but not to the corresponding region of a wild-type adhalin gene. In another aspect, the invention relates to methods for the detection of a mutation in the human adhalin gene which is responsible for primary adhalinopathy. Such methods include the use of the nucleic acid probes of the invention for detection of the myopathy by hybridization, as well as detection by direct DNA sequencing techniques.

DETAILED DESCRIPTION OF THE INVENTION

Figure 1:
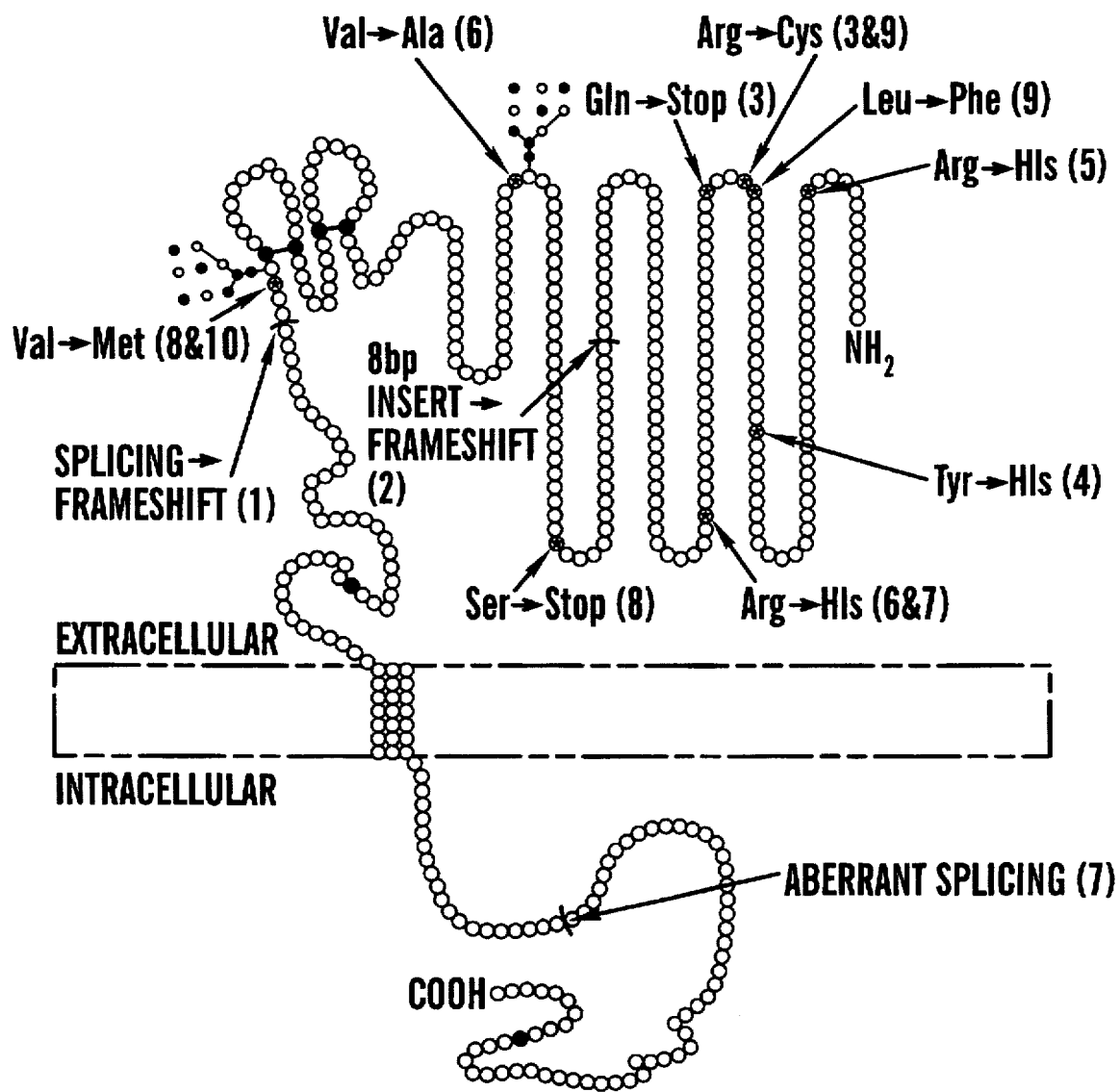
FIG. 1 is a diagrammatic representation which shows the positions of mutations in the adhalin protein. Each amino acid is represented by a circle (the first 23 amino acids, which represent the signal sequence, have been removed). Conserved extracellular cysteines (grey circle), a potential Ca/CaM-dependent protein kinase phosphorylation site (black circle), and potential N-linked glycosylation sites (branched chains) are indicated. Stars indicate missense or nonsense mutations. Black bars indicate sites interrupted by splice mutations or insertion. Numbers refer to the patients listed in tables. Asterisks indicate homozygous mutations.

The present invention is based on the discovery of genetic defects in the adhalin gene which result in primary adhalinopathy. More specifically, disclosed herein are nucleic acid probes which can be used to detect mutations within the adhalin gene which result in primary adhalinopathy. Primary adhalinopathy is one of two types of myopathies associated with adhalin deficiency. It is characterized by a mutation in the adhalin gene which has been mapped to chromosome 17q21. The second type is a myopathy wherein the absence of adhalin is secondary to a separate genetic defect involving a gene other than the adhalin gene.

The nucleic acid probes of the present invention are designed to enable the detection of a set of mutations which are specifically disclosed in the Exemplification section which follows. The probes hybridize specifically to a defined target sequence in a mutant adhalin gene, but not to the corresponding sequence in a wild-type adhalin gene, under stringent hybridization conditions. One of the possible sets of stringent hybridization conditions is 5×SSPE (1×SSPE is 0.15M NaCl, 1 mM Na-EDTA, 10 mM Naphosphate, pH 7.0), 5×Denhardt's solution (0.1% polyvinylpyrrolidone, 0.1% Ficoll, 0.1% BSA) at 45° C. Washing can then be carried out in 5×SSPE at 45° C.

More specifically, a set of 16 nucleic acid target sequences are disclosed. The set of 16 nucleic acid target sequences (referred to herein as SEQ ID NOS. 1, 3, 5, 7, 9, 11, 13, 15, 17, 19, 21, 23, 25, 27, 29 and 31) correspond to the mutations identified in Table 2 and elsewhere in the Exemplification section which follows. Given the identification of the 13 nucleic acid target sequences, it is a matter of routine experimentation to design nucleic acid probes which hybridize specifically to one member of the 13 target sequences, but not to the corresponding sequence in a wild-type adhalin gene under stringent hybridization conditions. Corresponding sequences in a wild-type adhalin gene allele are referred to herein as SEQ ID NOS. 2, 4, 6, 8, 10, 12, 14, 16, 18, 20, 22, 24, 26, 28, 30 and 32.

The design of oligonucleotide probes useful for the detection of a predetermined mutant sequence is a routine matter to one of skill in the art. Preferably, oligonucleotide probes range in size from about 10 nucleotides in length to about 30 nucleotides in length (longer probes can be used, but offer no substantial advantage over probes of the preferred size range). The nucleotide(s) of potential mismatch is centrally located in the design of the probe, and all other nucleotides in the oligonucleotide should be perfectly complementary with the target. The oligonucleotide probes can be designed to hybridize to either the sense strand, or the antisense strand, when using cDNA or DNA as a target.

The nucleic acid probes of the present invention are useful for the diagnosis of the myopathy in patients with an unknown form of muscular dystrophy. In addition, the probes can be used for diagnosis of the myopathy in presymptomatic individuals, and for prenatal diagnosis. Such diagnostic methods are performed by isolating nucleic acid from an individual and testing the diagnostic probes of the invention for the ability to hybridize to the isolated nucleic acid. For those mutations which fall within an exon sequence, the isolated nucleic acid can be genomic DNA, cDNA or mRNA which corresponds to the disclosed target. The isolated nucleic acid can be amplified, for example by the polymerase chain reaction, prior to hybridization diagnosis. As discussed above, the diagnostic hybridization is carried out under stringent hybridization conditions so that the diagnostic probes do not hybridize specifically to the corresponding wild-type sequence. In a preferred embodiment, the isolated nucleic acid is fixed to a solid support (e.g., nitrocellulose filter) using standard techniques.

In addition to the use of hybridization probes for the detection of primary adhalinopathy, the invention also relates to direct sequencing methods for determining such a myopathy. The cDNA sequence of the human adhalin gene has been published (Roberds et al., Cell 70:625 (1994)). By identifying flanking regions adjacent to the target regions identified in the present application, it is a routine matter to design primers which can be used to initiate DNA sequencing reactions. Such sequencing reactions can be used to determine whether the adhalin gene of an individual contains any of the mutations disclosed herein.

One convenient approach to the direct sequencing method is to isolate mRNA from muscle biopsy. cDNA is then produced from the mRNA, and the cDNA is amplified by the polymerase chain reaction. The amplified product is then sequenced using the dideoxy chain termination method.

A second convenient approach is to isolate genomic DNA and amplify exon sequences by the polymerase chain reaction. A cDNA probe complementary to the adhalin gene can be used to screen a genomic DNA library in order to identify genomic DNA clones which encode the adhalin gene. In order to amplify complete exon sequences, it is necessary to define primers which will hybridize specifically to intron sequences flanking the exons. This is accomplished by first determining the location of intron sequences in selected genomic DNA clones.

The most rapid way to determine the location of intron sequences in selected genomic clones is to employ primers within each of a pair of adjoining exons to amplify the intron between them. If this is unsuccessful (e.g., this can occur when an intron is extremely long), screening of a genomic library with exonic sequences should yield clones containing adjacent intron sequences. Sequencing primers are then designed which can be used to prime a sequencing reaction from the known exon sequences present in the cDNA into the unknown intron sequences. Intron sequence determined in this manner provides the sequence information necessary to design primers which are useful for amplifying the flanking exon sequences.

EXEMPLIFICATION

A total of 12 new independent cases of autosomal recessive muscular dystrophy from various origins (France, Italy, Germany, Algeria, Morocco) were examined. Five were familial cases; seven were sporadic. In all patients proximal muscles were predominantly affected and serum creatine-kinase levels were elevated, but the clinical pattern was of variable severity, ranging from severe childhood progressive muscular dystrophy to very mild forms with late-onset and minimal muscle impairment (Table 1). Intellectual development was normal in all cases. There was no heart dysfunction except in one family (#13) where two male siblings exhibited severe heart failure. In all patients but one (#2) muscle biopsy was performed, showing a typical necrosis-regeneration pattern of the muscle fibers, with variable degrees of the dystrophic process and connective tissue proliferation. In all these patients dystrophy was normal, whereas adhalin was deficient as judged by immunostaining of cryosections or western blot analysis. The deficiency varied from total absence of signal to some residual adhalin staining of normal size by western blot analysis (Table 1).

Linkage analysis was performed in one family from Algeria (#1) and one from Morocco (#2). Negative lodscores were obtained with the markers for the SCARMD locus on chromosome 13q and positive scores for the markers of the 17q21 region including the intragenic adhalin microsatellite (Allamand et al., Hum. Molec. Genet. 3:2269 (1994)). Mutation analyses were performed in patients from the two adhalin gene-linked families from North Africa, and in 10 European cases where linkage analysis was not possible: five from France (one familial and four sporadic), three sporadic cases from Italy and two familial cases from Germany (Table 1). The adhalin gene was explored by PCR amplification of genomic. DNA sequences corresponding to exons 1 to 8 and their flanking intronic sequences (representing altogether more than 95% of the coding sequence), followed by denaturing gradient gel electrophoresis (DGGE) analysis and direct sequencing. In all cases the parental origin of the mutation(s) was assessed and the segregation among the siblings established.

A variety of mutations was found in 18 out of the 24 chromosomes from the 12 new families explored, excluding the previously reported family #7 (Roberds et al., Cell 78:625 (1994); Romero et al., C. R. Acad. Sci. Paris 317: 70 (1994)) (Tables 1 & 2). In two patients (#12 and #13), no mutation was found. In these cases mutations may be located in the unexplored coding and non-coding sequences of the adhalin gene. Alternatively they may represent secondary adhalinopathies.

Among the ten new families with a mutated adhalin gene, four patients were homozygous: an inbred family from Morocco (#2), family #1 from Algeria with suspected consanguinity, and two European families without evidence of consanguinity, one from Germany (family #4), and one from Italy (family #6) (Table 2). In seven families the patients were compound heterozygotes. In one family (#11) only one abnormal allele was found.

Altogether, including the first reported family (#7) (Roberds et al., Cell 78: 625 (1994)), adhalin mutations were found on 21 chromosomes—two carried a nonsense mutation, two a duplication of 8 bp, three splice mutations affecting a critical G of an acceptor splice site, and 14 a missense mutation (Table 2). All substituted amino acid residues are conserved in rabbit and hamster adhalin except Val 175, which is Ile in rabbit (Roberds et al., J. Biol. Chem. 268: 23739 (1993)) and hamster. Each of the missense mutations segregated as a mendelian recessive trait. None was found in 160 control chromosomes, ruling out the possibility of these being common polymorphisms. Two polymorphic sequence variations were also found: CG→C A, at +27 in intron 1, and isosemantic GTC→GT T=Val(311)Val in exon 7.

The positions of the disease-related mutations in the protein are depicted in FIG. 1. Four out of the eight different missense mutations lie in exon 3, which may be a mutation hot-spot. Four missense mutations were C→T transversions affecting a methylable C. The recurrence of a given mutation on two or more unrelated chromosomes was observed for three different missense mutations (Table 2). One of them, Arg77Cys, was seen in four apparently unrelated chromosomes from two French and one German family.

Results demonstrated that primary adhalinopathies are not exceptional and are characterized by a broad spectrum of adhalin mutations, excluding a possible founder effect. They were found in patients from France, Germany, Italy, Algeria and Morocco, indicating that primary adhalinopathies are not geographically restricted. The two North African families provide the first evidence of primary adhalinopathy (chromosome17-linked) in populations where adhalinopathy was considered to be secondary because of linkage to chromosome 13 (Azibi et al., Hum. Molec. Genet. 2:1423 (1993); El Kerch et al., J. Med. Genet 31: 342 (1994); Ben Othmane et al., Nature Genet. 2: 315 (1992)). It will be important to determine the respective frequency of the two categories by genetic analysis, as there is no distinctive clinical, pathological or biological feature.

The clinical severity of primary adhalinopathies varies strikingly. The most severe clinical course was observed in patients in which adhalin was completely absent (Table 1) and who are homozygous for null mutations (Table 2), whereas missense mutations were observed in milder forms of variable severity. It is premature to define correlations between the nature or site of the mutation and phenotype, mostly because patients are often compound heterozygotes. The observed missense mutations caused a pronounced decrease of the amount of adhalin. Their possible impact on the level of transcript is currently being investigated. Missense adhalin mutations may also affect protein stability, either intrinsically or by perturbing essential sites of interaction with other protein(s). It is concluded that primary adhalinopathies are a significant cause of autosomal recessive myopathies and are geographically widespread. They may be caused by numerous different mutations, and may elicit muscular dystrophy of variable severity.

Methods

Morphological studies and immunostaining of cryosections.

Biopsies were obtained from all patients listed in Table 1 except in family #2. Cryosections were studied by histochemical and immunochemical methods as described (Matsumara et al., Nature 359: 320 (1992); Fardeau et al., C. R. Acad. Sci. Paris 316: 799 (1993); Romero et al., C. R. Acad. Sci. Paris 317: 70 (1994)). Monoclonal antibodies against adhalin (IVD3$_1$) (Matsumara et al., Nature 359: 320 (1992)) and dystrophin (NLC DYS2 and NLC DYS3, Novocastra) were used.

Immunoblot analysis.

Crude homogenates from muscle biopsy samples were prepared and processed essentially as described (Nicholson et al., J. Neurol. Sci. 94: 125 (1989)), except for the electrophoresis which was carried out in a homogeneous 10% SDS-polyacrylamide gel. Nitrocellulose blots were probed for dystrophin (using monoclonal antibodies DYS1 and DYS2, Novocastra) and adhalin (using affinity-purified polyclonal antibodies against adhalin fusion protein G and H17), and monoclonal antibody AdI/20A6 (raised against fusion protein G17). Antibodies were detected by enhanced chemoluminescence (ECL, Amersham).

Sequence analysis.

Genomic DNA extracted from blood or lymphoblastoid cell lines was analyzed by PCR using oligonucleotide primers flanking the intron-exon junctions exons 1–9 of the adhalin gene. After purification, the amplified product was sequenced on both strands using the same primers used for PCR amplification by the DyeDeoxy™ chain terminator method following the manufacturer's protocols (Applied Biosystem). When the sequence change affected or created a restriction site, the PCR product was digested with the appropriate restriction endonuclease and analyzed by agarose gel electrophoresis. Some mutations were also rechecked by ASO hybridization. DGGE analysis was performed using Lerman's algorithm and psoralen clamps as described (Fernandez et al., PCT Meth. & Applic. 3: 122 (1993)).

Note Regarding Additional Mutations.

In addition to the mutations listed in Table 2, 3 additional mutations have been identified which result in primary adhalinopathy:

Family GB

T to C (intron 7) wild-type GAGGGAAGGTGAATGTGGG SEQ ID NO:28 mutant GAGGGAAGGCGAATGTGGG SEQ ID NO:27

Family US

Deletion of 2 bp (964 & 965) wild-type ACAGGCTGAAGAGAGACCT SEQ ID NO:30 mutant CACAGGCTGGAGAGACCTG SEQ ID NO:29

Family (h)NA

A to T (intron 1) wild-type CTCGTGGGCAAGTTGGGCC SEQ ID NO:32 mutant CTCGTGGGCTAGTTGGGCC SEQ ID NO:31

TABLE 1

Clinical presentation and adhalin status in 13 families with autosomal recessive muscular dystrophy

| Family # | Origin | Number and sex of blot patients | Clinical onset | Age at loss of walk | Age in 1994 (clinical grade[a]) | Creatine kinase (age at test) | Adhalin[b] Immunofluorescence | Western blot |
|---|---|---|---|---|---|---|---|---|
| 1-MA | Algerian | 1:M | 6 y | 13 y | 20 y (10) | x4 (20 y) | 0 | 0 |
|  |  | 2:F | 6 y | 14 y | 19 y (10) | x8 (19 y) | 0 | 0 |
| 2-HA | Moroccan | 1:F | 9 y | 22 y | 30 y (10) | Elevated | Not done | Not done |
|  |  | 2:M | 7 y | 10 y | 28 y (10) | Elevated | Not done |  |
| 3-CH | French | 1:M | 9 y | 22 y | 13 y (7) | x100 (12 y) | 0 | Not done |
| 4-BE | German | 1:M | 4 y | No loss | 12 y (3) | x70 (12 y) | 0–1 | Not done |
|  |  | 2:M | 2 y | No loss | 10 y (2) | x90 (9 y) | 0–1 | Not done |
| 5-GA | French | 1:M | 8 y | 21 y | 24 y (6) | x32 (15 y) | 0/+ | + |
| 6-PE | Italian | 1:F | 7 y | No loss | 17 y (5) | x93 (9 y) | 0/+ | 0/+ |
| 7-HE[c] | French | 1:F | 12 y | No loss | 15 y (3) | x24 (14 y) | 0 | + |
|  |  | 2:F | 12 y | No loss | 15 y (3) | x24 (14 y) | 0 | + |
|  |  | 3:M | 9 y | No loss | 13 y (5) | x55 (12 y) | 0 | + |
|  |  | 4:F | None | No loss | 8 y (0) | x65 (7 y) | 0 | + |
|  |  | 1:F | None | No loss | 7 y (0) | x83 (64) |  | + |

TABLE 1-continued

Clinical presentation and adhalin status in 13 families with autosomal recessive muscular dystrophy

| Family # | Origin | Number and sex of blot patients | Clinical onset | Age at loss of walk | Age in 1994 (clinical grade[a]) | Creatine kinase (age at test) | Adhalin[b] Immuno- fluor- escence | Western blot |
|---|---|---|---|---|---|---|---|---|
| 8-ME | French | 1:M | 8 y | No loss | 36 y (4) | ×18 (27 y) | +/++ | + |
| 9-BER | Italian | 1:F | 12 y | No loss | 25 y (3) | ×27 (25 y) | + | + |
| 10-BA | French | 1:F | 12 y | No loss | 25 y (3) | ×30 (20 y) | ++ | + |
| 11-JO | French | 1:F | 12 y | No loss | 33 y (2) | ×15 (30 y) | ++ | ++ |
|  |  | 2:F | 15 y | No loss | 31 y (2) | ×17 (28 y) |  |  |
| *12-PA* | *Italian* | *1:F* | *6 y* | *No loss* | *14 y (5)* | *×49 (7 y)* | *0/+* | *++* |
| *13-LU* | *German* | *1:M[d]* | *6 y* | *10 y* | *At 11 y* | *×76 (10 y)* | *Not done* | *Not done* |
|  |  | *2:M[d]* | *6 y* | *No loss* | *10 y (3)* | *×49 (10 y)* | *0/+* | *+* |

Italics, cases in which no mutation was found in the adhalin gene. Families arranged in order of decreasing severity.
[a]Scored according to Walton's scale from 0 (no physical symptoms) to 10 (confined to bed) (Walton et al., Disorders of voluntary muscle. 6th edn (Churchill Livingstone, Edinburgh 1994)).
[b]Intensity of immunostaining was visually estimated (normal signal scored ++++).
[c]This family has already been reported (Roberds et al., Cell 78: 625 (1994); Romero et al., C.R. Acad. Sci. Paris 317: 70 (1994)).
[d]Case with prominent cardiomyopathy.

TABLE 2

Mutations in the adhalin gene

|  | Family # | Mutation and position in each allele | Consequences (codon number) |
|---|---|---|---|
| Severe phenotype | 1-MA | AG → AA (−1 exon 7) | Aberrant splicing[a] |
|  |  | AG → AA (−1 exon 7) | Aberrant splicing[a] |
|  | 2-HA | Insertion of 8 bp (exon 5) | Frameshift |
|  |  | Insertion of 8 bp (exon 5) | Frameshift |
|  | 3-CH | CAG → TAG (exon 3) | Nonsense (80) |
|  |  | CGC → TGC (exon 3) | Arg77Cys[d] |
| Intermediate phenotype | 4-BE | CGC → TGC (exon 3) | Arg77Cys[d] |
|  |  | CGC → TGC (exon 3) | Arg77Cys[d] |
|  | 5-GA | TAC → CAC (exon 3) | Tyr62His |
|  |  | GTT → GCT (exon 6) | Val242Ala |
|  | 6-PE | CgT → CAT (exon 2) | Arg34His |
|  |  | CGT → CAT (exon 2) | Arg34His |
| Moderate phenotype | 7-HE[c] | CGT → CAT (exon 3) | Arg98His[d] |
|  |  | TCA → CCA (exon 5) | Val175Ala |
|  | 8-ME | CGT → CAT (exon 3) | Arg98His[d] |
|  |  | AG → AT (−1 exon 8) | Aberrant splicing[b] |
|  | 9-BER | TCA → TGA (exon 5) | Nonsense (151) |
|  |  | GTG → ATG (exon 6) | Val247Met[d] |
| Mild phenotype | 10-BA | CGC → TGC (exon 3) | Arg77Cys[d] |
|  |  | GGA → GAA (exon 3) | Gly68Gln |
|  | 11-JO | GTG → ATG (exon 6) | Val247Met[d] |
|  |  | (2nd mutation not found) |  |

[a]Expected skipping of exon 7 (out of frame).
[b]Expected skipping of exon 8 (in frame).
[c]This family has already been reported (Matsumara et al., Nature 359: 320 (1992); Romero et al., C.R. Acad. Sci. Paris 317: 70 (1994)).
[d]Mutations observed in two or more unrelated families.

We claim:
1. A method for detecting a mutation in the human adhalin gene which is associated with muscular dystrophy, comprising:
- a) providing a nucleic acid sample isolated from an individual to be tested for the mutation;
- b) contacting the nucleic acid sample from step a) with a nucleic acid probe selected from the group consisting of: SEQ ID NOS.: 1, 3, 5, 7, 9, 11, 13, 19, 21, 23, 25, 27, 29 and 31 which hybridizes specifically to the mutant form of the adhalin gene, but not to the wild-type form of the adhalin gene; and
- c) detecting specific hybridization of the nucleic acid probe to the mutant form of the adhalin gene.

* * * * *

UNITED STATES PATENT AND TRADEMARK OFFICE
CERTIFICATE OF CORRECTION

PATENT NO. : 5,733,732
DATED : March 31, 1998
INVENTOR(S) : Campbell et al.

It is certified that error appears in the above-indentified patent and that said Letters Patent is hereby corrected as shown below:

ON THE TITLE PAGE:
Item [73] Please add;

-- Institut National de la Sante et de la Recherche Medicale, Paris, France --.

Signed and Sealed this

Twenty-seventh Day of March, 2001

Attest:

NICHOLAS P. GODICI

Attesting Officer    Acting Director of the United States Patent and Trademark Office

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:1:

CTCTGTGCAA GTGGATAAG                                    19

( 2 ) INFORMATION FOR SEQ ID NO:2:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:2:

CTCTGTGCAG GTGGATAAG                                    19

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:3:

CAAGCCACCA AGCCGAGTTC                                   20

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:4:

ATACCAAGCC GAGTTCCTGG                                   20

( 2 ) INFORMATION FOR SEQ ID NO:5:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:5:

CGCTACACCT AGCGCAGCC     19

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

CGCTACACCC AGCGCAGCC     19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

CGGTGGCTCT GCTACACCC     19

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

CGGTGGCTCC GCTACACCC     19

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

CACATCACCC ACCACGCCC     19

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

CACATCACCT ACCACGCCC     19

(2) INFORMATION FOR SEQ ID NO:11:

( i ) SEQUENCE CHARACTERISTICS:
   ( A ) LENGTH: 19 base pairs
   ( B ) TYPE: nucleic acid
   ( C ) STRANDEDNESS: double
   ( D ) TOPOLOGY: linear ( i i ) MOLECULE TYPE: DNA (genomic)

( x i ) SEQUENCE DESCRIPTION: SEQ ID NO:11:

ACTTCCGCGC TGACTGGTG        19

( 2 ) INFORMATION FOR SEQ ID NO:12:

( i ) SEQUENCE CHARACTERISTICS:
      ( A ) LENGTH: 19 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:12:

ACTTCCGCGT TGACTGGTG        19

( 2 ) INFORMATION FOR SEQ ID NO:13:

( i ) SEQUENCE CHARACTERISTICS:
      ( A ) LENGTH: 19 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:13:

TTGTGGGCCA TGTCTTTGT        19

( 2 ) INFORMATION FOR SEQ ID NO:14:

( i ) SEQUENCE CHARACTERISTICS:
      ( A ) LENGTH: 19 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:14:

TTGTGGGCCG TGTCTTTGT        19

( 2 ) INFORMATION FOR SEQ ID NO:15:

( i ) SEQUENCE CHARACTERISTICS:
      ( A ) LENGTH: 19 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:15:

CAGAAGATCA TGGGCTCCA        19

( 2 ) INFORMATION FOR SEQ ID NO:16:

( i ) SEQUENCE CHARACTERISTICS:
      ( A ) LENGTH: 19 base pairs
      ( B ) TYPE: nucleic acid
      ( C ) STRANDEDNESS: double
      ( D ) TOPOLOGY: linear (ii) MOLECULE TYPE: DNA (genomic)

(xi) SEQUENCE DESCRIPTION: SEQ ID NO:16:

CAGAAGATCG TGGGCTCCA                    19

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

TGCTCAACGC CACCTCTGC                    19

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

TGCTCAACGT CACCTCTGC                    19

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

TTTTCCACAT GCTGAAGAG                    19

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:20:

TTTTCCACAG GCTGAAGAG                    19

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:21:

TGCTGCCCTG AACACCTGC    19

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:22:

TGCTGCCCTC AACACCTGC    19

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:23:

TGGTGCAATA TGACCCTGG    19

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:24:

TGGTGCAATG TGACCCTGG    19

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:25:

ACCTCCAGGA ACACCCAGA    19

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:26:

ACCTCCAGGG ACACCCAGA    19

(2) INFORMATION FOR SEQ ID NO:27:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:27:

GAGGGAAGGC GAATGTGGG    19

( 2 ) INFORMATION FOR SEQ ID NO:28:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:28:

GAGGGAAGGT GAATGTGGG    19

( 2 ) INFORMATION FOR SEQ ID NO:29:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:29:

CACAGGCTGG AGAGACCTG    19

( 2 ) INFORMATION FOR SEQ ID NO:30:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:30:

ACAGGCTGAA GAGAGACCT    19

( 2 ) INFORMATION FOR SEQ ID NO:31:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:31:

CTCGTGGGCT AGTTGGGCC    19

( 2 ) INFORMATION FOR SEQ ID NO:32:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear (  i  i  ) MOLECULE TYPE: DNA (genomic)

(  x  i  ) SEQUENCE DESCRIPTION: SEQ ID NO:32:

CTCGTGGGCA AGTTGGGCC 19